United States Patent [19]

Wu et al.

[11] Patent Number: 5,130,653
[45] Date of Patent: Jul. 14, 1992

[54] APPARATUS FOR DETECTING SURFACE FLAWS IN CYLINDRICAL ARTICLES

[75] Inventors: Samuel C. Wu, Lakewood, Colo.; Satish S. Udpa, Ames, Iowa; Jeffrey S. Weaver, Fort Collins; George M. Hnatiuk, Loveland, both of Colo.

[73] Assignee: Coors Brewing Company, Golden, Colo.

[21] Appl. No.: 569,187

[22] Filed: Aug. 17, 1990

[51] Int. Cl.⁵ .................. G01N 27/82; B07C 5/344
[52] U.S. Cl. .................. 324/241; 209/567; 209/598; 324/232; 324/233
[58] Field of Search .............. 324/226, 227, 236–243, 324/207.17, 207.18, 207.19; 209/567, 570, 598

[56] References Cited

U.S. PATENT DOCUMENTS

| | | | |
|---|---|---|---|
| 3,686,564 | 8/1972 | Mallick, Jr. et al. | 324/245 X |
| 3,694,740 | 9/1972 | Bergstrand | 324/240 X |
| 3,786,672 | 1/1974 | Gaerttner | 324/243 X |
| 3,916,301 | 10/1975 | Vild et al. | 324/226 |
| 4,002,966 | 1/1977 | Hinds et al. | |
| 4,029,958 | 6/1977 | Wright | |
| 4,042,877 | 8/1977 | Sieverin | |
| 4,212,205 | 7/1980 | West et al. | |
| 4,241,821 | 12/1980 | Wu et al. | |
| 4,569,445 | 2/1986 | Kovats et al. | 324/662 X |
| 4,742,298 | 5/1988 | Ando et al. | 324/242 X |

Primary Examiner—Kenneth A. Wieder
Assistant Examiner—Warren S. Edmonds
Attorney, Agent, or Firm—Klaas, Law, O'Meara & Malkin

[57] ABSTRACT

Apparatus for detecting surface flaws in cylindrical articles having central longitudinal axes, including a guide assembly for guiding the cylindrical articles along a displacement path having a central longitudinal axis extending coaxially of the central longitudinal axes of the articles and a detection coil assembly positioned in annular relationship with the displacement path for producing a signal representative of the surface geometry of a cylindrical article which traverses the displacement path.

7 Claims, 6 Drawing Sheets

APPARATUS FOR DETECTING SURFACE FLAWS IN CYLINDRICAL ARTICLES

BACKGROUND OF THE INVENTION

The present invention relates generally to the detection of surface flaws in manufactured articles and, more particularly, to the detection of surface flaws in cylindrically shaped articles such as can bodies.

Apparatus for detecting surface flaws in cylindrical objects are disclosed in U.S. Pat. Nos. 4,002,966; 4,029,958; 4,042,877; and 4,212,205, which are each hereby specifically incorporated by reference for all that is disclosed therein.

U.S. Pat. No. 4,212,205 of West et al. discloses a container defect detection apparatus which magnetically strikes containers causing them to ring at their natural frequency. A microphone senses the resonance; a bandpass filter filters out known frequencies generated by a known acceptable container. The energy of predetermined frequencies associated with defective containers is examined and compared with a threshold level to detect defects.

U.S. Pat. No. 4,002,966 of Hinds et al. discloses a method for detecting imperfections on the wall of cylindrical containers which includes generating a magnetic field having a predetermined value by passing an alternating current through an inductor means and then rotating a container body about its axis to pass all portions of a selected section of container body to be tested through the magnetic field while maintaining a fixed spacing between the tested portion of the container body and the inductor means and then comparing the rms value of the current producing the magnetic field with a reference value, and producing a signal when there is a predetermined difference between the two values.

U.S. Pat. No. 4,029,958 of Wright describes an apparatus for inspecting containers wherein a stream of cylindrical metal containers is fed into apparatus having a rotatable turret. The turret indexes each container past a driven wheel for imparting rotation thereto. A proximity detector disposed in close conjunction with the periphery of the rotating container detects any substantial runout of the periphery, indicating a dented container. A pair of elongated eddy current type transducers aligned axially along the sidewall of a juxtaposed rotating container are specifically described for use as a proximity detector.

U.S. Pat. No. 4,042,877 of Sieverin discloses a method of providing a substantially uniform gap between detection means and a substantially cylindrical object while it is being rotated in an inspection station formed by portions of the arcs of the circumferences of a pair of drive wheels mounted on a rotatably driven first shaft, and a pair of wheels mounted on a rotatably driven second shaft parallel to the first shaft.

U.S. Pat. No. 4,241,281 of Wu et al. discloses an apparatus for receiving used metallic containers and for dispensing a token or the like for the value of the container received. An object inserted into the apparatus passes through a control tube assembly which includes first and second inductive-type metal sensor units having coaxially aligned cylindrical passages and a third photoelectric-type sensor unit. The sensor units are arranged axially spaced apart and adjusted to the lengths of cans which are to be received. The first sensor unit provides a signal indicative of the passage of any metallic object; the second sensor unit provides a signal indicative of the passage of an aluminum object of predetermined minimum axial length; and the third sensor unit provides a signal indicative of the passage of any object of a predetermined minimum axial length. This patent is not directed to surface inspection of articles.

Thus, with exception of U.S. Pat. No. 4,212,205 which employs acoustic inspection techniques, the prior art relating to cylindrical article inspection apparatus teaches that a cylindrical article to be inspected for surface flaws is rotated within the sensing field of a sensor which is positioned alongside the article.

OBJECT OF THE INVENTION

It is an object of the present invention to provide an inspection method and apparatus which enables an article to be inspected without rotation.

It is another object of the invention to provide an inspection method and apparatus which enables a cylindrical article to be inspected during axial displacement of the article.

It is another object of the invention to provide an inspection apparatus and method which employs two excitation coils and two sensor coils in the differential mode.

It is another object of the invention to provide an inspection apparatus and method which utilizes eddy currents set up in a cylindrical article during axial passage of the article through a magnetic field for the purpose of detecting surface variations in the article.

SUMMARY OF THE INVENTION

The present invention may comprise apparatus for detecting surface flaws in cylindrical articles having central longitudinal axes, including a guide assembly for guiding the cylindrical articles along a displacement path having a central longitudinal axis extending coaxially of the central longitudinal axes of the articles and a detection coil assembly positioned in annular relationship with the displacement path for producing a signal representative of the surface geometry of a cylindrical article which traverses the displacement path.

The invention may also comprise a method of generating data representative of the surface geometry of a cylindrical article including the steps of: passing a first alternating current through a first electrical coil; passing a second alternating current in same phase relationship with the first alternating current through a second electrical coil; passing the cylindrical article through the first and second electrical coils; detecting the magnetic flux in the proximity of the first coil during the passage of the cylindrical article through the first coil; detecting the magnetic flux in the proximity of the second coil simultaneously with the detection of flux in the proximity of the first coil; comparing the detected magnetic flux of the first coil to the detected magnetic flux of the second coil and generating a data signal representative of that comparison.

BRIEF DESCRIPTION OF THE DRAWINGS

An illustrative and presently preferred embodiment of the invention is shown in the accompanying drawings in which.

DETAILED DESCRIPTION OF THE INVENTION

Appendices

Computer software and system setup procedures for one embodiment of the invention which is presently the best mode known is set forth in the attached Appendices A-D which form a part of the Specification of this patent application.

Apparatus In General

Figure 1:
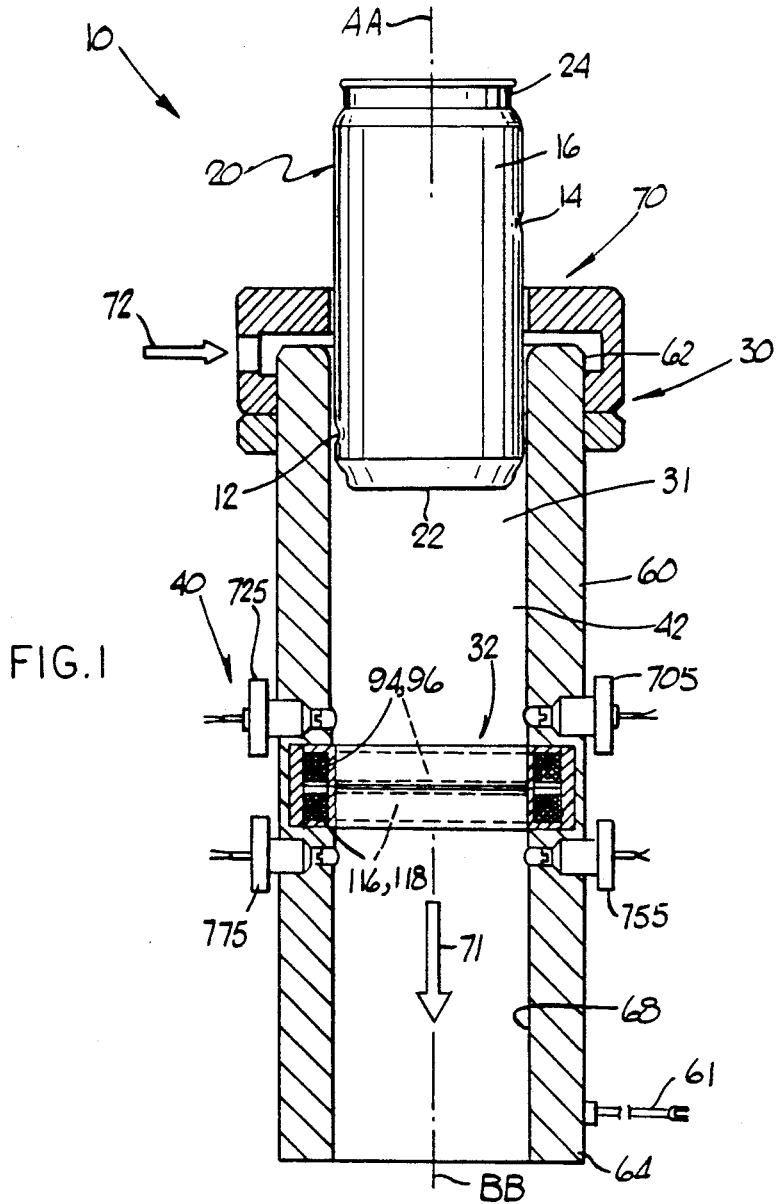
FIG. 1 is a partially cross-sectional elevation view of an apparatus for detecting surface flaws in cylindrical articles.

FIG. 1 illustrates an apparatus 10 for detecting surface flaws such as dents 12, 14 in the surface 16 of a cylindrical object such as an aluminum can body 20 having a central cylindrical axis AA extending between a first axial end 22 and a second axial end 24 thereof. The apparatus 10 comprises an axial guide path assembly 30 which guides cylindrical articles 20 along an article displacement path 31 having a central longitudinal axis BB. The articles 20 are guided along the path 31 with the central longitudinal axis AA of each article aligned coaxially with the central longitudinal axis BB of the path.

The apparatus 10 comprises a detection coil assembly 32 positioned in annular relationship with the displacement path 31. The coil assembly produces a signal representative of the surface geometry of a cylindrical article 20 which traverses the displacement path 31.

Figure 2:
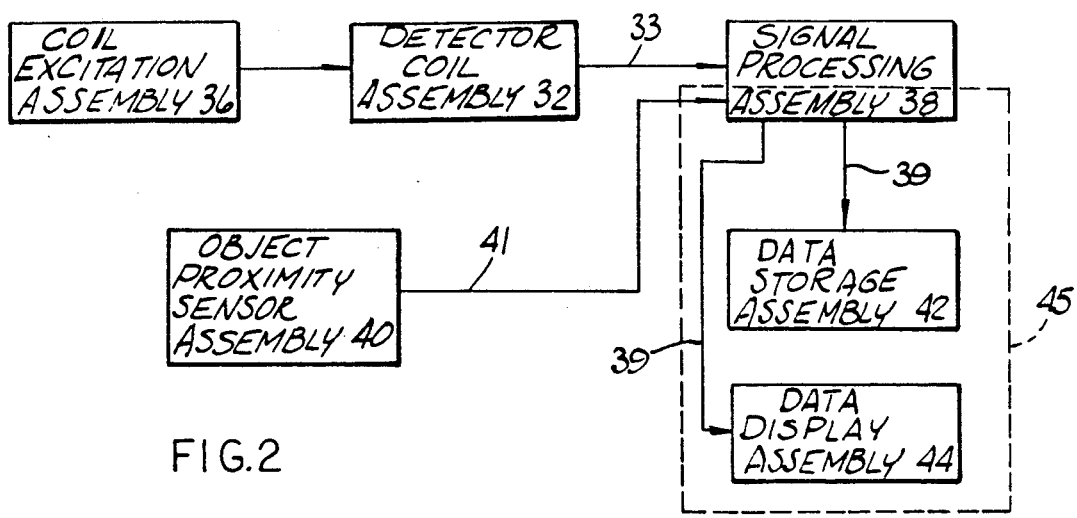
FIG. 2 is a block diagram of the major electronic and electrical components of the apparatus of FIG. 1.

A coil exciter assembly 36, FIG. 2, is connected to the detector coil assembly 32 and provides excitation energy thereto. A signal processing assembly 38 is connected to the detector coil assembly 32 and processes a signal 33 generated by the detector coil assembly 32.

An article sensor assembly 40 is provided along the article displacement path 31. Assembly 40 detects the presence or absence of a cylindrical article 20 within a predetermined length region of the displacement path in which the detector coil assembly 32 is located and generates a signal 41 indicative of the presence or absence of a cylindrical article within this region.

Signal 41 is provided to the signal processing assembly 38 which processes this signal and the signal 33 from the detector coil assembly 32 and generates a signal 39 indicative of the surface geometry of a cylindrical object 20 which has traversed the article displacement path 31.

Signal 39 may be provided to a data storage assembly 42 such as the hard disk of a microcomputer assembly 45 and/or may be provided to a data display assembly 44 such as the video display of a computer 45 or a printer connected to a computer assembly 45.

As indicated schematically in FIG. 2, a portion of the signal processing assembly 38 may comprise hard-wired electrical components, and another portion of the signal processing assembly 38 may comprise the software of a computer assembly 45. Alternatively, signal processing assembly 38 might consist entirely of hard-wired components.

Having thus described the invention in general, specific features of the invention will now be described in further detail.

Axial Guide Path Assembly

As illustrated in FIG. 1, axial guide path assembly 30 may comprise a nonferromagnetic tubular member 60, which may be aluminum, having an infeed end 62, a discharge end 64, and a central cylindrical cavity 66 extending between the infeed end 62 and the discharge end 64. The cavity 66 is defined by an interior wall 68 which may have a diameter, e.g. 78 mm, which is slightly larger, e.g. 1.0 mm larger, than the diameter of an article 20 which is to be inspected. In one embodiment of the invention, three elongate axially extending strips of paper (not shown) are provided adjacent to the interior wall 68 to facilitate centering of an object 20 which is passed through cylindrical cavity 66. Member 60 is preferably grounded, as by wire 61, to eliminate the buildup of static electricity.

In another embodiment of the invention, which is presently the best mode contemplated, an air bearing assembly 70 which receives air from a pressurized air source 72 is provided at the infeed end 62 of tubular member 60 and provides an annular air flow adjacent to interior surface 68 which serves to center a cylindrical article 20 as it passes through cavity 66. The direction of the airflow as indicated at 71 is preferably in alignment with the force of gravity which pulls the article 20 through the fixedly positioned steel member 60.

Detector Coil Assembly

Figure 3:
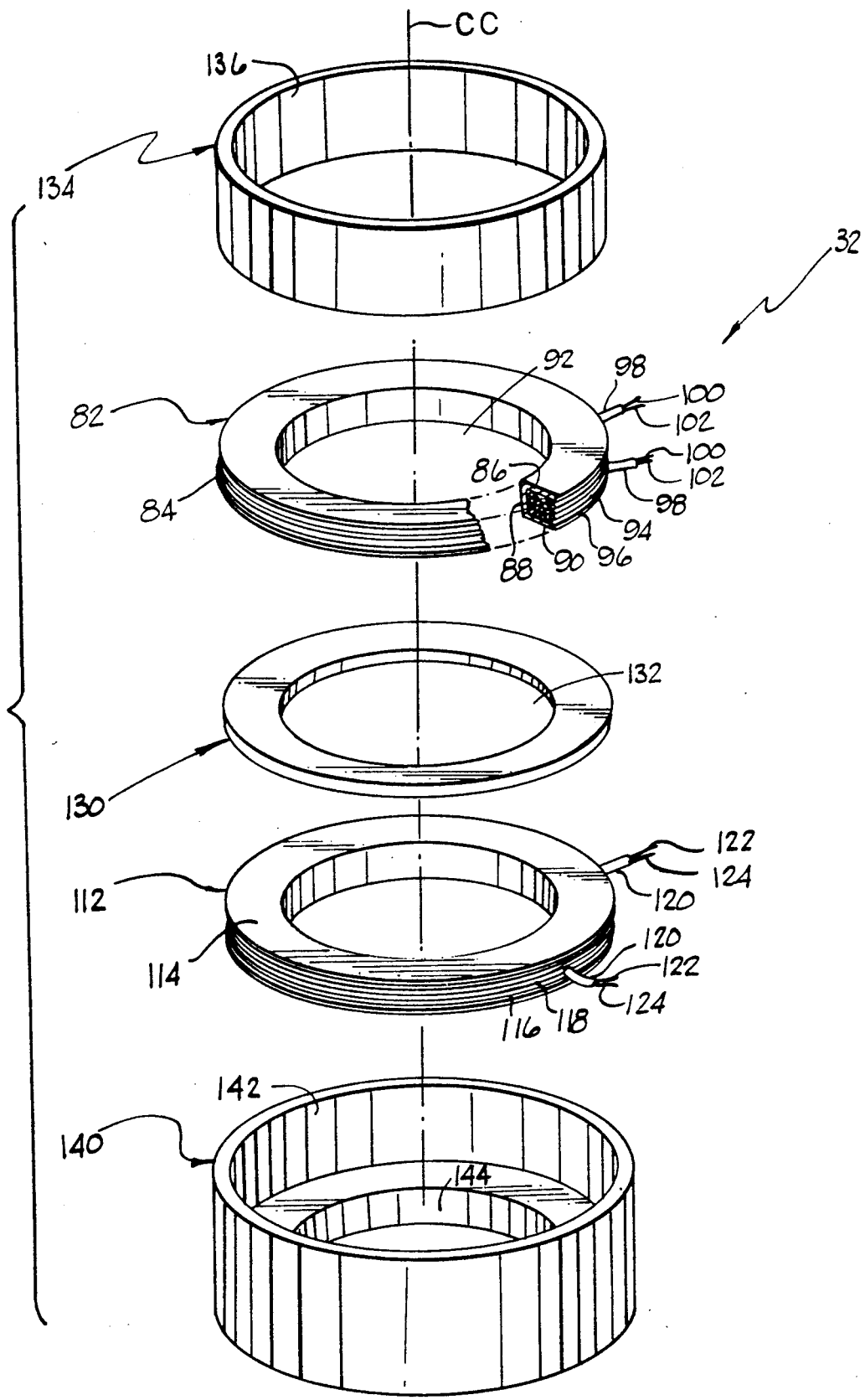
FIG. 3 is an exploded perspective view of a detector coil assembly of the apparatus of FIG. 1.

As illustrated in FIG. 3, detector coil assembly 32 comprises a first spool assembly 82 which includes a plastic spool member 84 having an upper radially extending flange portion 86, an axially extending tubular portion 88 connected to the upper flange portion, and a lower radially extending flange portion 90 connected to the tubular portion. A central axial cavity 92 extends through the spool member 84 and may have the same diameter as cavity 66 of tubular member 60. Flanges 86, 90 may each have an axial thickness of 1 mm and may have an outer diameter of 77.9 mm. Axial portion 88 may have an axial length of 2 mm and may have a radial thickness of 0.5 mm. A first excitation coil 94 and a first sensor coil 96 are provided by a bifilar cable 98 which is wound about the spool axially extending portion 88. The bifilar cable or winding pair 98 comprises a first wire 100 corresponding to the excitation coil and a second wire 102 corresponding to the sensor coil. In one exemplary embodiment, bifilar cable 98 is a No. 40 enameled magnetic wire which is wound in 300 turns about spool axially extending portion 88.

A second spool assembly 112 is provided comprising a plastic spool member 114 which may be identical in size and construction to spool member 84, and comprising a second excitation coil 116 and a second sensor coil 118 which are provided by a second bifilar cable 120 with a first wire 122 corresponding to the excitation coil 116 and a second wire 124 corresponding to the sensor coil 118.

A ferromagnetic spacer ring member 130, which may have an axial dimension of 1.6 mm, is provided which is positioned in abutting relationship with the lower flange 90 of spool 84 and the upper flange of second spool 114. Ring member 130 has a cylindrical hole 132 extending therethrough having a diameter equal to the diameter of the cavities of the spool members.

An outer ring member 134, which may have a wall thickness of 2 mm, has an internal diameter approximately equal to the external diameters of the spool members 84, 114 and ring member 130. The axial length of the outer ring member 134, which may be 12 mm, is equal to the combined axial lengths of the spool members 84, 114 and the ring member 134. Each of the spool members 84, 114 and the ring members 130, 134 may be constructed from steel.

A holder member 140, which may be constructed from a non-conductive material such as delrin plastic, comprises an upper, larger diameter cavity 142 having a diameter and axial length approximately equal to the outer diameter and axial length of outer ring 134. Holder member 140 has a lower, smaller diameter cavity 144 having a diameter equal to the diameter of spool cavity 92.

The spool members and spacer ring member are mounted within the outer ring member 134, and the outer ring member 134 is in turn mounted within upper cavity 142 of holder member 140. Holder member 140 is mounted within a cavity at an axial midportion of tubular steel member 60 with the central longitudinal axis CC thereof positioned in coaxial relationship with the central longitudinal axis BB of the tubular member cavity 66. The tubular member 60 may comprise two separate axial portions which facilitates the mounting of holder 140 therewithin.

Coil Excitation Assembly In General

Figure 4:
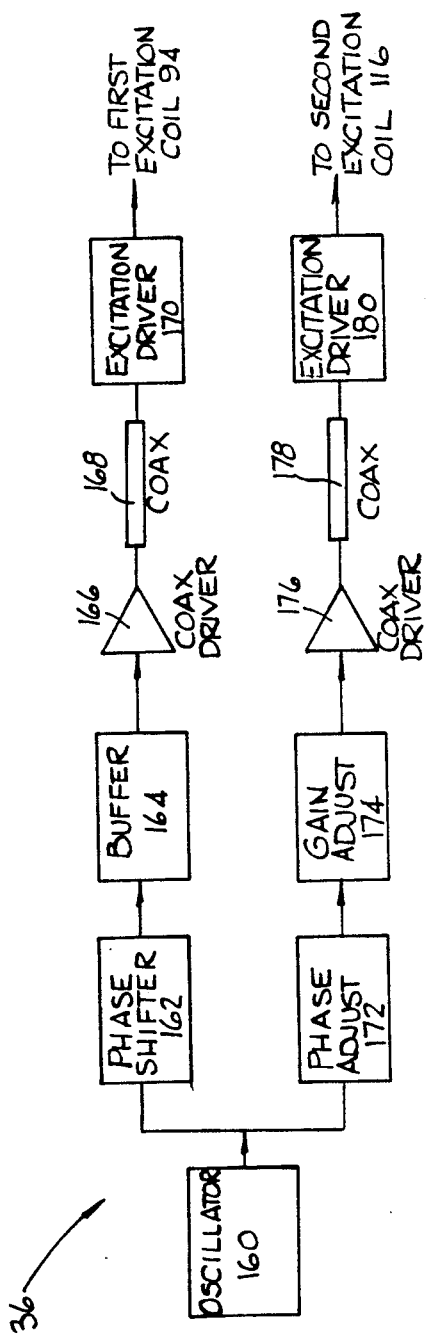
FIG. 4 is a block diagram of a coil excitation assembly for the apparatus of FIG. 1.

As illustrated in FIG. 4, coil excitation assembly 36 may comprise an oscillator circuit 160 which provides a signal to a phase shifter circuit 162 which in turn provides a signal to a buffer circuit 164. The buffer circuit provides a signal to a coax driver circuit 166 which transmits the signal through a coaxial cable 168 to an excitation driver circuit 170 which in turn transmits the signal to first excitation coil 94.

The oscillator circuit 160 also provides a signal to a phase adjustment circuit 172 which in turn provides a signal to a gain adjustment circuit 174. The gain adjustment circuit provides a signal to a coax driver circuit 176 which transmits a signal through coaxial cable 178 to an excitation driver circuit 180. The excitation driver circuit 180 transmits a signal to second excitation coil 116.

Signal Processing Assembly In General

Figure 5:
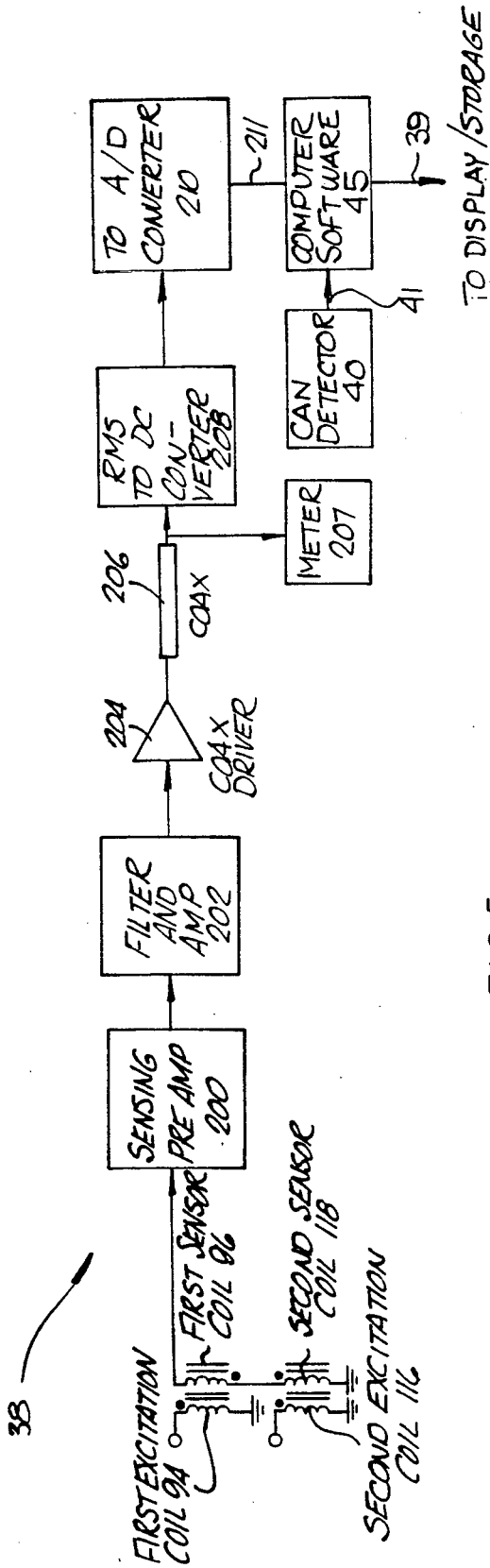
FIG. 5 is a block diagram of a signal processing assembly for the apparatus of FIG. 1.

As illustrated in FIG. 5, signal processing assembly 38 comprises a first sensor coil 96 and second sensor coil 118 connected in differential opposition. Second sensor coil 118 is connected at one terminal thereof to ground and is connected at the other terminal thereof to one terminal of first sensor coil 96. First sensor coil 96 has the second terminal thereof connected to a sensing preamplifier circuit 200. The sensing preamplifier circuit 200, in response to a signal from the sensor coils 96, 118, provides a signal to filter and amplifier circuit 202 which in turn provides a signal to coax driver circuit 204. The coax driver circuit provides a signal which is transmitted through coaxial cable 206 to an RMS-to-DC converter 208 and also to an operator viewable analog meter 207. Converter 208 provides a signal to A/D converter 210 which in turn provides a signal 211 to signal processing software of a computer 45. The signal processing software of computer 45 also receives an article detection signal 41 from article detection assembly 40 as described in further detail below. Software within the computer processes the signal 211 from the coils 96, 118 and signal 41 from the article detector and generates a data signal 39 indicative of the surface geometry of a container 20 passed through the apparatus 10. Data signal 39 may be provided to a display device to provide a graphic or numeric display of the information representative of article geometry or may be provided to a data storage device for storing such data.

Circuitry In Detail

Figure 6:
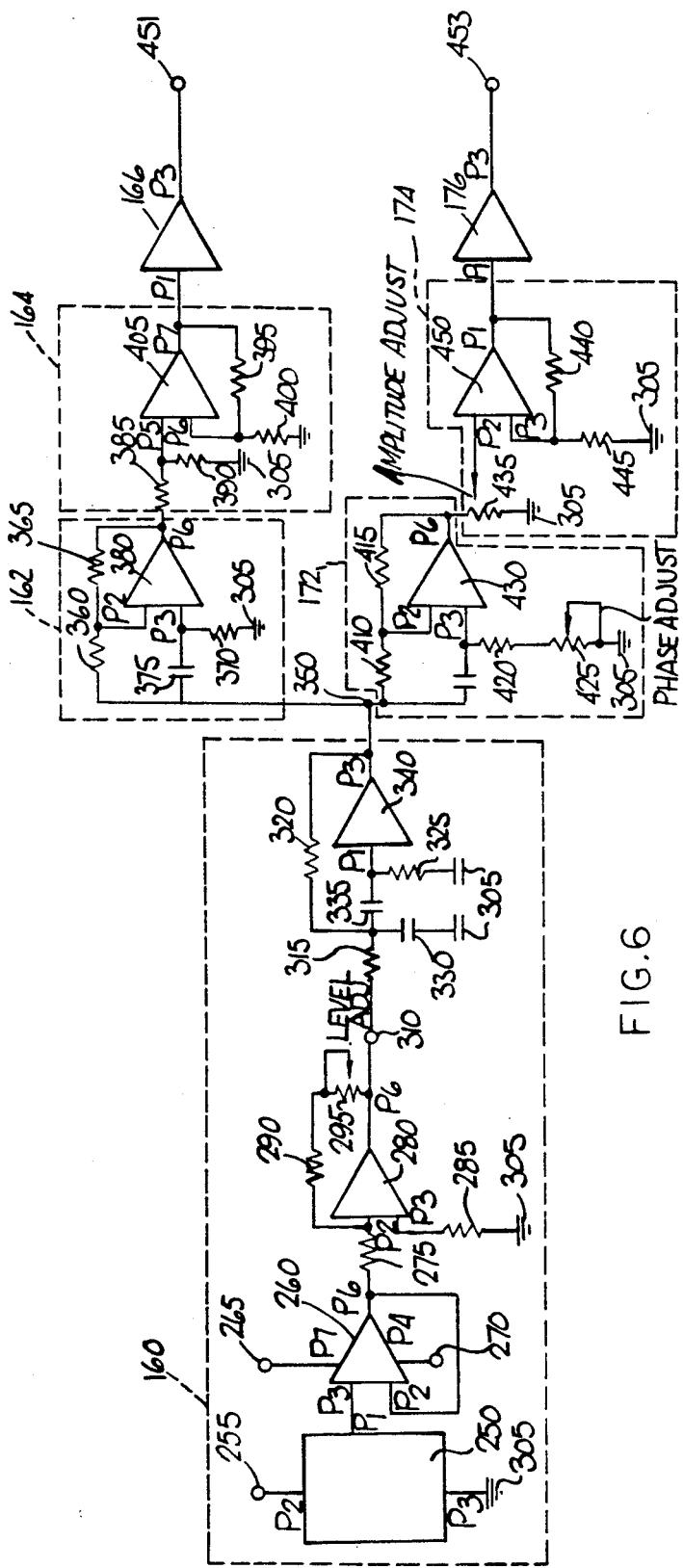
FIG. 6 is a detailed circuit diagram of a portion of the coil excitation assembly of FIG. 4.

As illustrated in FIG. 6, oscillator circuit 160 may comprise a crystal oscillator 250 which may be of the type commercially available from Vectron Laboratories, Inc. of 166 Glover Avenue, Norwalk, Conn., 06856-9979, as Model No. CO-252827. The pin connections of crystal oscillator 250 and other electronic components illustrated in FIGS. 6–11 are represented by the designation P. The crystal oscillator 250 is provided in a circuit which includes ground 305, +15 volt power source 255, an LM318AN op amp 260, a +15 volt power source 265, a −15 volt power source 270, a 1000 ohm resistor 275, an LM318AN op amp 280, a 1000 ohm resistor 285, a 3300 ohm resistor 290, and a 5000 ohm variable resistance level adjuster 295. The oscillator circuit also comprises a 6980 ohm resistor 315, an 887 ohm resistor 320, a 6980 ohm resistor 325, a 690 pF capacitor 330, a 680 pF capacitor 335, and an LT1010CH high capacity buffer 340. The oscillator circuit provides an output to connector node 350 which is also connected to phase shifter circuit 162, which will now be discussed.

Phase shifter circuit 162 may comprise a 1000 ohm resistor 360, a 1000 ohm resistor 365, a 1580 ohm resistor 370, a 1 nF capacitor 375, and an LM318AN op amp 380.

As further illustrated in FIG. 6, buffer circuit 164, which is connected to phase shifter circuit 162, may comprise a 546 ohm resistor 385, a 511 ohm resistor 390, a 2000 ohm resistor 395, a 2000 ohm resistor 400, and an LF412AN dual op amp 405.

As further illustrated in FIG. 6, coax driver circuit 166 may comprise an LT1010CH high capacity buffer.

As further illustrated in FIG. 6, phase adjustment circuit 172 is connected to node 350 and may comprise a 1000 ohm resistor 410, a 1000 ohm resistor 415, a 1100 ohm resistor 420, a 5000 ohm variable resistance phase adjuster 425, and an LM318AN op amp 430.

As further illustrated in FIG. 6, gain adjustment circuit 174 may comprise a 10,000 ohm variable resistance amplitude adjuster 435; a 2000 ohm resistor 440; a 2000 ohm resistor 445; and an LF412AN dual op amp 450.

As further illustrated in FIG. 6, coax driver circuit 176 may be an LT1010CH high capacity buffer 176. Coax driver circuits 166 and 176 provide outputs 451, 453, respectively.

Figure 7:
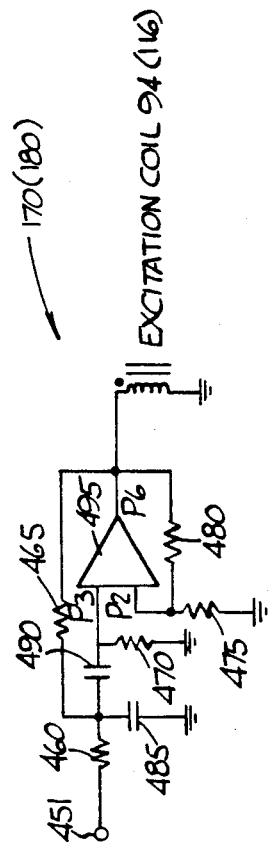
FIG. 7 is a detailed circuit diagram of another portion of the coil excitation assembly of FIG. 4.

Output 451 from coax driver circuit 166 is shown in FIG. 7 which specifically illustrates an embodiment of first excitation driver circuit 170. First excitation driver circuit 170 and second excitation driver circuit 180 may be identical and are thus not both described. Referring now to FIG. 7, it will be seen that first excitation driver circuit comprises a 3320 ohm resistor 460, a 3320 ohm resistor 465, a 3320 ohm resistor 470, a 2000 ohm resistor 475, a 3320 ohm resistor 480, a 680 pF capacitor 485, a 680 pF capacitor 490, and an LM318AN op amp 495.

Figure 8:
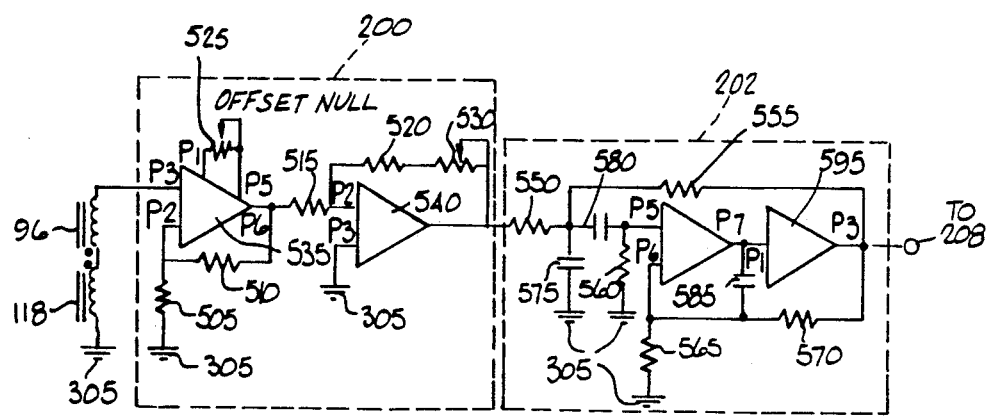
FIG. 8 is a detailed circuit diagram of a portion of the signal processing assembly of FIG. 5.

As illustrated in FIG. 8, sensing amplifier circuit 200 may comprise a 20 ohm resistor 505; a 2000 ohm resistor 510, a 2000 ohm resistor 515; a 2000 ohm resistor 520; a 2000 ohm variable resistance offset null 525; a 20,000 ohm variable resistance preamp gain 530; an LT1028CN high band width, low noise op amp 535; and an LF412AN dual op amp 540.

As further illustrated in FIG. 8, filter and amplifier circuit 202 may comprise a 3320 ohm resistor 550, a 3320 ohm resistor 555, a 3320 ohm resistor 560, a 3320 ohm resistor 570, a 680 pF capacitor 575, a 680 pF capacitor 580, a 100 pF capacitor 585, an LF412AN dual op amp 590, and an LT1010CH high capacity buffer 595.

Figure 9:
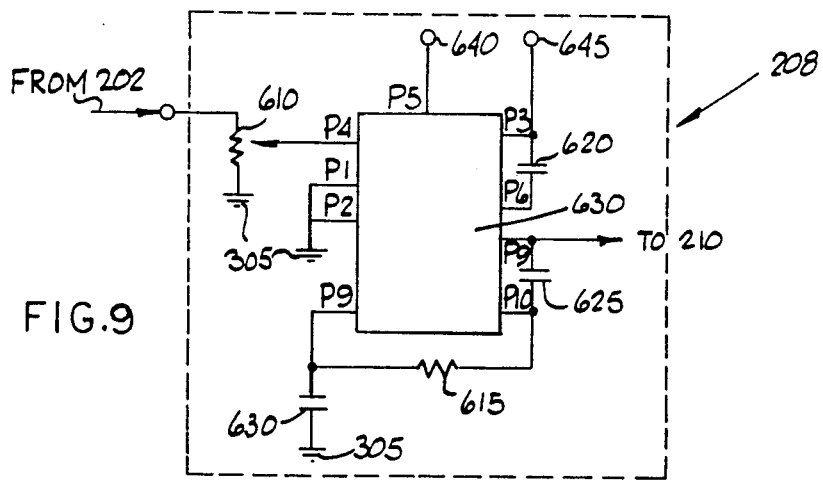
FIG. 9 is a detailed circuit diagram of another portion of the signal processing assembly of FIG. 5.

As illustrated in FIG. 9, RMS-to-DC converter 208 may comprise a 10,000 ohm variable resistance level adjuster 610; a 24,900 ohm resistor 615; a 5.0 nF capacitor 620; a 5.0 nF capacitor 625; a 222 pF capacitor 630; an AD536JH RMS-to-DC converter 635; a −15 volt power source 640; and a +15 volt power source 645.

Figure 10:
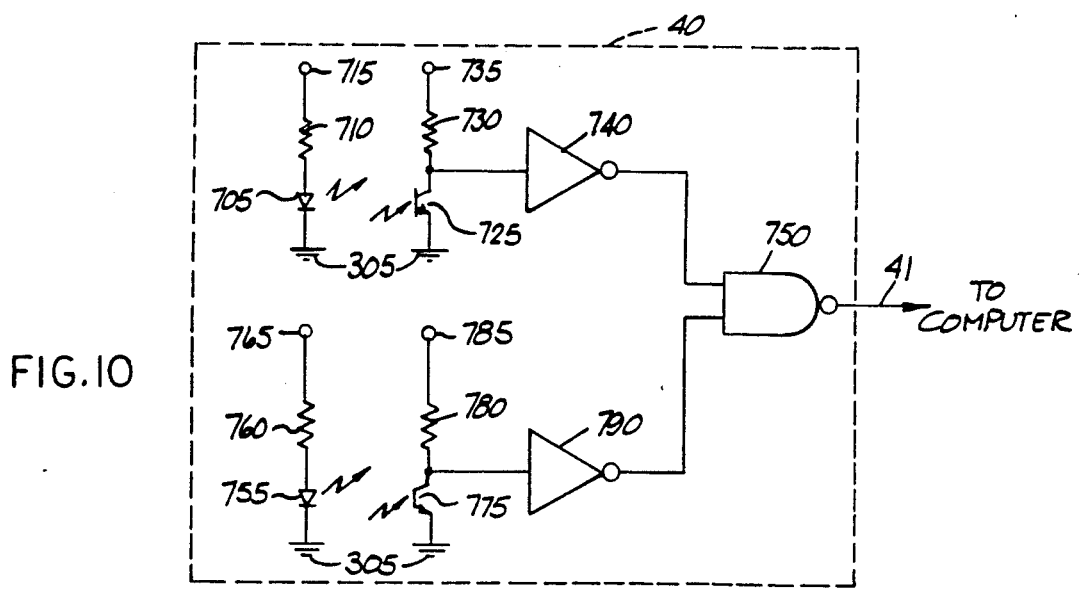
FIG. 10 is a detailed circuit diagram of an object proximity sensor assembly.

As illustrated in FIGS. 1 and 10, article sensor assembly 40 may comprise an SET8703-001 high output infrared LED 705; a 10,000 ohm resistor 710; a +15 volt power supply 715; an SDP8403-301 infrared phototransistor 725; a 10,000 ohm resistor 730; a +5 volt power source 735; a 74LS14 Hex Schmidt Trigger Inverter 740; and a 74LS00 Quad NAND Gate. The article sensor assembly 40 further comprises a second LED 755, a second resistor 750, a second 15 volt power supply 765, a second phototransistor 775, a second resistor 780, a second 5 volt power source 785, and a second Hex Schmidt Trigger Inverter 790 which each correspond identically to the components described in the immediately preceding sentence. The NAND gate 750 provides an article detection signal 41 which is high when an article is positioned within the proximity of detector coil assembly 32 and which is low whenever no article is present. Thus, in the arrangement shown in FIG. 1, a can 20 is indicated to be present only when both phototransistors 725, 775 are covered by the can.

The electronic components described above are readily commercially available from a number of vendors. Table 1 indicates one commercial source for a number of the above-described components.

TABLE 1

| | |
|---|---|
| LM318 | National Semiconductor Corporation, 2900 Semiconductor Drive, Santa Clara, California, 95051. |
| LF412 | National Semiconductor Corporation, 2900 Semiconductor Drive, Santa Clara, California, 95051. |
| LM7805 | National Semiconductor Corporation, 2900 Semiconductor Drive, Santa Clara, California, 95051. |
| 74LS00 | National Semiconductor Corporation, 2900 Semiconductor Drive, Santa Clara, Caliornia, 95051. |
| 74LS14 | National Semiconductor Corporation, 2900 Semiconductor Drive, Santa Clara, California, 95051. |
| LT1010 | Linear Technology Corporation, 1630 McCarthy Blvd., Milpitas, California, 95035. |
| LT1028 | Linear Technology Corporation, 1630 McCarthy Blvd., Milpitas, California, 95035. |
| AD536 | Analog Devices, Inc., One Technology Way, P.O. Box 9106, Norwood, Massachusetts, 02062-9106. |

Computer Software

Specific computer software for processing signal 39 from the signal processing assembly 38 is set forth in the Appendices.

Figure 11:
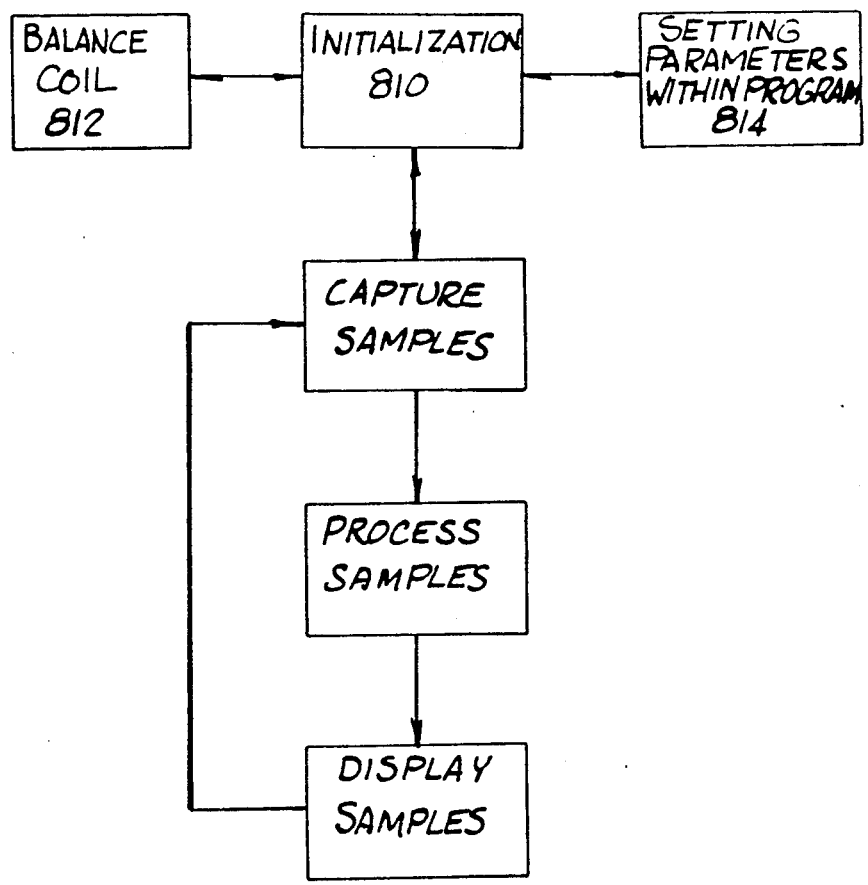
FIG. 11 is a block diagram illustrating software operations performed by a computer assembly portion of the signal processing assembly of FIG. 5.

FIG. 11 illustrates the general operations performed by the computer software. The software at initialization goes through a coil balancing operation and also has certain program parameters set through operator input. The program captures signal 39 samples of a duration defined by signal 41. These samples are processed to remove noise, etc. and are then displayed.

Sample Display

Figure 12:
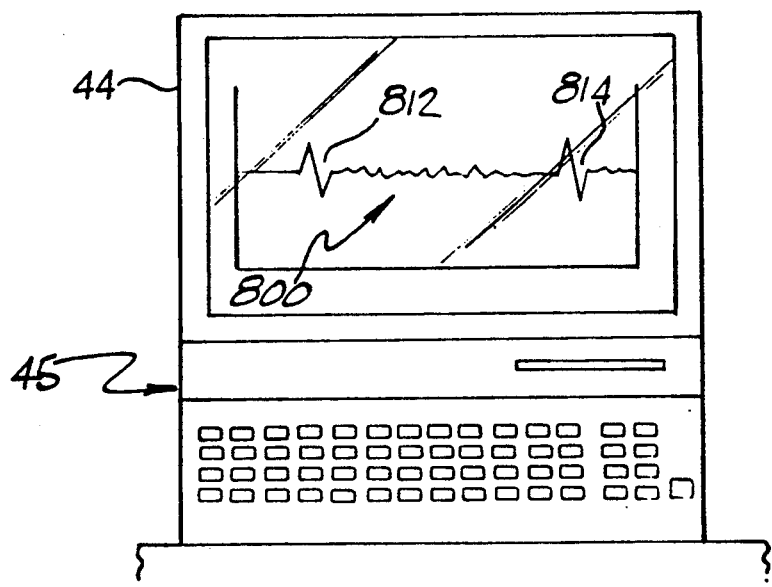
FIG. 12 is a front elevation view of a computer assembly with a signal display which is representative of the surface geometry of a cylindrical object which has passed through the apparatus of FIG. 1.

A typical sample display such as may be provided on a conventional computer assembly 45 display screen 44 is illustrated in FIG. 12. The signal display 41 in this particular format is flat in the regions corresponding to the smooth surface portions of can body 20 but has a double spike configuration 812, 814 in the regions corresponding to the dented regions 12, 14 of the can body. In this illustrated embodiment, the can body detector sensor assembly 40 has been so positioned as to truncate signal 39 in a manner such that the leading and trailing edge portions 22, 24 of the can body, which are of differing diameter from the remainder of the can body, are not represented in the signal display.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

APPENDICES A-D

A Appendix

Software Description

This section describes the use of the software supplied with the can tester, and includes installation instructions and system operating procedures.

Installation

The program which operates the can tester is called cap.exe. It will run on any IBM pc with at least 512 k of memory and CGA graphics. Before cap can be run, however, a Data Translation DT2821 series A/D card must be installed in the system. This basically entails configuring the card for bipolar operation with all other parameters set to factory defaults and inserting the card into the PC. For further details on the DT2821 series installation procedures, refer to the DT2821 manual.

To install cap.exe, simply copy the executable file to whichever directory you will be operating from. Also copy the two files, cap.cfg and cap.idx to the same directory. These two files contain the start-up parameters and index weights.

Software Description

To run the program, type: cap at the dos prompt. The program will load, and the defaults will be set from the file cap.cfg. A listing of the configuration file is included in appendix E, and is documented and self-explanatory.

You will be presented with the main menu. A list of the menu options and a description of each follows:

Balance Coil This option continuously shows the magnitude of the signal output from the can tester. To achieve good sensitivity, the displayed value must be minimized by adjusting the knobs on the can tester box. The procedure for accomplishing this is covered below.

Capture Data This option causes the program to enter the capture mode. A different screen is displayed. The capture mode screen contains a graph of signal amplitude vs. length along the can. Every time a can is dropped through the canon, the resulting signal is shown on the graph. Dents, cracks, and other abnormalities are displayed as peaks on the graph. The position of a peak in the graph corresponds approximately to the position of a defect on the can. Positioning is not exact because the can accelerates under gravity as it travels through the canon. If the save mode is turned on, the graph is saved to disk when the can is dropped. To exit the capture mode, press the ESCAPE key. One warning: don't insert a balancing can into the coil while in the Capture Data mode, or the PC will hang. This is because no maximum sample limit is included in the sampling routines, and it is possible to overwrite program memory if a can is left in the coil for too long. This will not cause any problems under normal operation.

Set Parameters This option displays a menu of parameters which may be set as desired. A list of the available options and their description follows:

Set Plotting Maximum The graph shown in the capture mode has a default range of ±200 units. This option allows the range to be set to any desired value. Entering 0 for the plotting maximum will cause the graphing routines to automatically scale the graph to correspond to the maximum absolute value found in each set of samples.

Toggle Processed/Raw Display This option allows the viewing of either raw sampled data, or data which has been processed after it was sampled.

Enter Save-File Name Cap has the capability to save buffers to disk so that hardcopy plots, statistical analysis, or other desired processing may be done. To use this feature, it is necessary to enter a file name. Any valid DOS file name may be used with the exception of cap.exe (if you used that name, the program would destroy itself). If it is desired to use a file in a directory different from the default directory, a path may be entered in the standard DOS syntax. The total length of the path and file name must be less than 40 characters. Entering a file name activates the other file options described below. If no file name is entered; i.e. the ENTER key is pressed, the file name will be cleared and the save mode exited.

Toggle Save-File Write Mode After a file name has been entered, the mode used to write to the file should be specified. The default write mode is append, which means that each time the buffer is saved to the file, The new data is stored at the end of the file. By selecting this option, the mode is changed to truncate, which means that all previous information in the file is destroyed. The write mode may be toggled back and forth as desired.

Toggle Save-to-Disk Mode Selecting this option turns on the save mode. This will cause the displayed buffer contents to be written to the specified file every time a can is sent through the canon. The save mode may be turned on and off as desired.

Set Sample Frequency This option allows you to alter the frequency at which the A/D converter samples data. Frequencies should be entered as over the range of 0.5 Hz to 50 KHz. When the program is started, the sample frequency defaults to 2500 Hz.

Set Filter Order This option allows setting the order of the averaging filter applied to the data in the process mode. Typically, this parameter should be between 2 and 10.

Set A/D Gain This option changes the gain the A/D card uses when it samples. Sensitivity is enhanced if the A/D Gain is set to its maximum value of 8; however extremely good can tosses are necessary to being the signal amplitude low enough to not saturate the A/D. Experimentation is recommended.

Set Out of Balance Threshold This parameter, which may be set anywhere between 0 and 4095, controls how far the system must be out of balance before the software detects it.

To exit the program, hit the ESCAPE key when the main menu is displayed.

B Appendix

Balancing Procedure

The sensing coil of the can tester is configured as a bridge. This requires that the bridge be balanced to null out the signal and sensitize the system to any defects. Because of the extreme sensitivity of the system, balancing must be performed carefully and meticulously to achieve maximum performance.

Standard Balancing Procedure

The following series of steps should result in nearly perfect balance:

1. Turn on the can tester and allow the system to come to thermal equilibrium (approx. one hour). This is necessary to eliminate drift errors in the instrumentation.
2. Insert a calibration can into the canon and adjust its position so that the can is as centered in the bore as possible.
3. Set the adjustment knobs (425, 435, FIG. 6) to mid-scale. Observe the meter (207, FIG. 5) on the panel. The reading should be something less than full scale; if it is not, carefully tweak the adjustment knobs in very small increments until a dip is observed.
4. Now, carefully adjust the amplitude and phase knobs until the meter reads the minimum value. At this point, the system is very near balance.
5. Run the cap program, and select the "Balance Coil" option. Very carefully tweak the adjustment knobs to minimize the displayed number.

Now the system is balanced, and the calibration can may be removed. Keeping the system balanced will ensure the maximum sensitivity to defects.

C Appendix — Program Configuration File

The following is an example *cap.cfg* file. It demonstrates how the program start-up defaults may be set as desired.

```
# CAP.CFG - configuration file for the cap program.  This file allows setting
# defaults when the program starts.  Lines beginning with '#' are comments.
# Parameters are given in lowercase, and the valid parameters are:
#       frequency, fname, save, trunc, max, process, order, adc_gain, and
#       threshold.
# The comments below may be helpful to understand how these work.

# the frequency may be set from 1 to 50e3 Hz.  Without this line, the default
# frequency is 2.5 KHz
frequency 20000 to default to no filename, put a '#' in front of the next line
fname test.fil to default to no-save to disk mode, comment the next line out
save

# If the following line is commented out, the file mode is append
#trunc

# Plotting maximum
max 750

# Filter order (1 to 100)
order 10

# Analog to Digital converter gain
adc_gain 4

# Threshold must be > 0 and < 4095
threshold 3000 if the following line is commented out, the raw signal will be displayed.
if not commented, the signal will be processed before display.
process
```

D Appendix — Program Source Code

The following pages contain the source code for the *cap* program. The program was written in Microsoft C, and will compile with the Microsoft C compiler or with Microsoft QuickC.

(dt2821.h)

```
/* base I/O address for registers */
#define DT2821_BASE 0x240

/* register map */

/* control/status register */
#define ADCSR (DT2821_BASE)
```

```c
/* channel list control/status */
#define CHANCSR (DT2821_BASE + 2)

/* A/D Data register */
#define ADDAT (DT2821_BASE + 4)

/* D/A control/status register (not on DT2824-PGH or PGL models) */
#define DACSR (DT2821_BASE + 6)

/* D/A data register (not on DT2824-PGH or PGL models) */
#define DADAT (DT2821_BASE + 8)

/* digital I/O data register */
#define DIODAT (DT2821_BASE + 0x0a)

/* supervisory control/status register */
#define SUPCSR (DT2821_BASE + 0x0c)

/* pacer clock register */
#define TMRCTR (DT2821_BASE + 0x0e)

/* register bit assignments */
/* ADCSR */
#define ADERR     0x8000
#define ADCLK     0x0200
#define MUXBUSY   0x0100
#define ADDONE    0x0080
#define IADDONE   0x0040
#define GS_MSK    0x0030
#define GS_1      0x0000
#define GS_2      0x0010
#define GS_4      0x0020
#define GS_8      0x0030
define CHAN_MSK  0x000f /* CHANCSR */
define LLE         0x8000
#define PRESLA_MSK  0x0f00
define NUMB_MSK    0x000f /* ADDATA */
define ADDATA_MSK 0x0fff /* DACSR (not on 2824-PGH and PGL models) */ define DAERR    0x8000
define YSEL     0x0200
#define SSEL     0x0100
#define DACRDY   0x0080
#define IDARDY   0x0040
#define DACLK    0x0020
#define HBOE     0x0002
#define LBOE     0x0001

/* DADATA (not on 2824-PGH and PGL models) */
#define DADATA_MSK 0x0fff

/* DIODAT */
#define HI_MSK  0xff00
#define LO_MSK  0x00ff

/* SUPCSR */
#define DMAD    0x8000
```

```
#define ERRINTEN      0x4000
#define CLRDMADONE    0x2000
#define DDMA          0x1000
#define DS_NONE       0x0000
#define DS_ADCLK      0x0400
#define DS_DACLK      0x0800
#define DS_ADTSCAN    0x0c00
#define DS_MSK        0x0c00
#define BUFFB         0x0200
#define SCDN          0x0100
#define DACON         0x0080
#define ADCINIT       0x0040
#define DACINIT       0x0020
#define PRLD          0x0010
#define STRIG         0x0008
#define XTRIG         0x0004
#define XCLK          0x0002
#define BDINIT        0x0001

/* TMRCTR */
#define PRSCL_MSK     0x0f00
#define CNT_MSK       0x00ff
```

(cap.c)

```
/* vi: set autoindent showmatch : */ include <stdio.h>
include <conio.h>
include <string.h>
#include "dt2821.h"

#define enable_clk()  outpw(DIODAT,0x0100)
#define disable_clk() outpw(DIODAT,0x0000)

define BUFFER_LENGTH 10000 int bs;                         /* number of samples taken */
int buffer[BUFFER_LENGTH];      /* A/D sample buffer */
int gbuf[BUFFER_LENGTH];        /* graphing buffer (holds processed data) */
float x[BUFFER_LENGTH];         /* processing buffer */ extern double freq;
extern int adc_gain,order,threshold;
extern int index1[10],index2[10],index3[10];
double idx1,idx2,idx3;

int balance_coil()
{
int v;
char ptmp[10];

clr_disp();
    center_text(5,"Please insert a good can into the canon and adjust the");
    center_text(6,"potentiometers to minimize the displayed value.");
    prompt_line("(hit any key when finished)");
    disp_text(12,20,"value:");
    init_adc_polled(2.0,adc_gain);

/* enable A/D clock */
    outpw(DACSR,HBOE);
    enable_clk();
```

```c
    do {
        sample_adc(&v);
        sprintf(ptmp,"%4d",v);
        disp_text(12,27,ptmp);

} while(!kbhit());
    getch();

disable_clk();

return(0);
} int process_buffer(b,bufsize,g,np)

int *b,bufsize,*g,*np;
{
float sum;
register int i,j;
int *t,*t1,*t2;
int status;

status = 0;

/* check for balance */
    /* find the first point where the value is < threshold */
    for(t = b,i = 0; *t > threshold && i < bufsize; t++,i++);

/* if none found, we're out of balance */
    if(i == bufsize) status = 1;

/* find the first pt from the rt where value < threshold */
    for(t1 = b + bufsize - 1; *t1 > threshold; t1--);

/* the pt should be significantly > the first pt */
    if((long)t1 <= (long)t + (long)(bufsize/4)) status = 1;

/* also, the value should not saturate between t & t1 */
    for(t2 = t; *t2 < 4095 && t2 < t1; t2++);
    if(t2 != t1) status = 1;

t = b;

/* compute the avg of the data set */
    for(i = 0,sum = 0.0; i < bufsize; i++) sum += t[i];

sum /= bufsize;

/* copy the data to the graphing buffer, subtracting the avg */
    for(i = 0; i < bufsize; i++)
        x[i] = (float)t[i] - sum;

/* make sure we have enough samples to filter them */
    *np = bufsize;
    if(*np < 5) status = 1;

/* nth order moving window filter */
    *np -= order;
    for(i = 0; i < *np; i++) {
        for(j = 1, sum = x[i]; j <= order; j++) sum += x[i+j];
        x[i] = sum / (order + 1);
    }
```

```c
    /* difference the data to remove linear trend */
    *np -= 2;
    for(i = 0; i < *np; i++)
        x[i] = x[i+2] - 2*x[i+1] + x[i];

/* nth order moving window filter */
    *np -= order;
    for(i = 0; i < *np; i++) {
        for(j = 1, sum = x[i]; j <= order; j++) sum += x[i+j];
        x[i] = sum / (order + 1);
    }

/* gain of 10 */
    for(i = 0; i < *np; i++)
        g[i] = (int) (100.0 * x[i]);

return(status);
} int compute_index(b,n)
int *b,n;
{
register int i;
int step;
int val;

if(n < 10) return(-1);
    step = n/10;

idx1 = idx2 = idx3 = 0;
    for(i = 0; i < n; i++) {
        val = (b[i] > 0 ? b[i] : -b[i]);
        idx1 += index1[i/step] * val;
        idx2 += index2[i/step] * val;
        idx3 += index3[i/step] * val;
    }
    idx1 /= n;
    idx2 /= n;
    idx3 /= n;

return(0);
} int capture_data()
{
register int i;
int status;

/* get the converter ready to sample */
    init_adc_polled(freq,adc_gain);

/* perform the conversion */
    status = read_buffer(buffer,&bs);
    if(status == -1) {
        gprompt_line("error in A/D conversion (hit <CR>)");
        getch();
        return(0);
    } if(status == -2) {
        getch();
        return(-1);
    }
```

```c
/* only if configured for bipolar */
#if 0
        /* transform the buffer from offset binary to 2's complement */
        for(i = 0; i < bs; i++)
            buffer[i] -= 0x800;
endif return(0);
} int show_labels(t,b)
char *t,*b;
{
char ptmp[80];

gclr_line(17);
        gclr_line(18);
        sprintf(ptmp,"   current top label: %s",*t? t: "(none)");
        gdisp_text(17,5,ptmp);
        sprintf(ptmp,"current bottom label: %s",*b? b: "(none)");
        gdisp_text(18,5,ptmp);

return(0);
} int save_buffer(b,n,fname,trunc)
int *b,n,trunc;
char *fname;
{
FILE *fp;
int i;
char ptmp[80];
int min,max;
static char tlabel[80] = "";
static char blabel[80] = "";
static char oldfname[40] = "";
static int samplecnt = 0;

/* check if save is really desired */
        gprompt_line("save sampled data? (y/n)");
        if(getch() == 'n') return(0);

if(strcmp(fname,oldfname)) {
            samplecnt = 0;
            strcpy(oldfname,fname);
        }

/* display current labels and values */
        show_labels(tlabel,blabel);
        max = -32768;
        min = 32767;
        for(i = 0; i < n; i++) {
            if(b[i] < min) min = b[i];
            if(b[i] > max) max = b[i];
        }
        sprintf(ptmp,"xmin: %d xmax: %d ymin: %d ymax: %d",0,n-1,min,max);
        gdisp_text(19,5,ptmp);
        gclr_line(20);
        sprintf(ptmp,"Sample #%d",samplecnt);
        gdisp_text(20,5,ptmp);
```

```
/* check that current labels are okay */
gprompt_line("enter new top label, or <CR> to continue");
gmv_curs(17,27);
gets(ptmp);

if(*ptmp) {
        strcpy(tlabel,ptmp);
        show_labels(tlabel,blabel);
    } gprompt_line("enter new bottom label, or <CR> to continue");
    gmv_curs(18,27);
    gets(ptmp);

if(*ptmp) {
        strcpy(blabel,ptmp);
        show_labels(tlabel,blabel);
    }

/* open the file */
    if(trunc)
        fp = fopen(fname,"w");
    else if(!access(fname,0))
        fp = fopen(fname,"a");
    else
        fp = fopen(fname,"w");

if(!fp) {
        close_graphics();
        sprintf(ptmp,"unable to open capture file: %s (hit <CR>)",fname);
        prompt_line(ptmp);
        getch();
        return(-1);
    }

/* go to the end of file */
    fseek(fp,0L,2);
    fprintf(fp,"Sample #%d %s\n",samplecnt++,tlabel);
    fprintf(fp,"%s\n",blabel);
    fprintf(fp,"%d %d %d %d\n",0,n-1,min,max);

fprintf(fp,"%d\n",n);
    for(i = 0; i < n; i++)
        fprintf(fp,"%5d\n",b[i]);
    fclose(fp);

gclr_line(24);
    return(0);
} int capture_mode(fname,save,trunc,max,process)
char *fname;
int save, trunc, max, process;
{
register int i;
int first,nplt;
char ptmp[80];
int cap_status;

open_graphics();
```

```
/* first time through, only display the screen; don't capture */
first = 1;
cap_status = 0;
do {
   if(!first) { cap_status = 0;
        if(capture_data() < 0) {
            close_graphics();
            return(0);
        } gclr_line(15);
        gclr_line(24);
        gdisp_text(15,5,"PROCESSING...");

/* do any needed processing on the buffer */
        if(process) {
            cap_status = process_buffer(buffer,bs,gbuf,&nplt);
        } else {
            for(i = 0; i < bs; i++)
                gbuf[i] = buffer[i];
            nplt = bs;
        }

} else {
        /* display screen only first time through */
        nplt = 1;
        for(i = 0; i < bs; i++) {
            buffer[1] = 1;
            gbuf[1] = 1;
        }
    }

/* graph the result */
    gclr_disp();
    plot(gbuf,nplt,max);
    gcenter_text(13,"Signal Amplitude vs. Can Length");
    if(cap_status) {
        fputc('\a',stdout);
        gdisp_text(15,5,"System out of balance or bad toss");
    } else
        gdisp_text(15,5,"Sample displayed.");
    compute_index(gbuf,nplt);
    sprintf(ptmp,"Index 1: %lg",idx1);
    gdisp_text(16,5,ptmp);
    sprintf(ptmp,"Index 2: %lg",idx2);
    gdisp_text(16,30,ptmp);
    sprintf(ptmp,"Index 3: %lg",idx3);
    gdisp_text(16,55,ptmp);

if(save&&!first)
        if(save_buffer(gbuf,nplt,fname,trunc) < 0)
            return(0);

gdisp_text(24,19,"Waiting for Trigger... (hit <ESC> to quit)");
    first = 0;
} while(1);
}
```

(capmain.c)

```c
/* vi: set autoindent showmatch : */
include <stdio.h>
include <conio.h>
include <string.h> extern unsigned bs;

char fname[40];
int save = 0;
int trunc = 0;
int max = 750;
int process = 0;
double freq = 2500.0;
int order = 10;
int adc_gain = 4;
int threshold = 3000;
int index1[10];
int index2[10];
int index3[10];

int load_cfg()
{
static char cfg_fname[13] = "cap.cfg";
char ptmp[80],line[80],cmd[40],*p;
int tmp,lcnt;
double dtmp;
FILE *fp;

/* attempt to open file */
    prompt_line("opening configuration file...");
    fp = fopen(cfg_fname,"r");
    if(!fp) {
        sprintf(ptmp,"unable to open configuration file: %s. (hit <CR>)",
            cfg_fname);
        prompt_line(ptmp);
        getch();
        return(-1);
    }
    /* read the settings from the configuration file */
    prompt_line("setting parameters from configuration file...");
    lcnt = 0;
    while(1) {
        /* get the next line */
        fgets(line,80,fp);
        if(feof(fp)) {
            prompt_line("parameters read.");
            fclose(fp);
            return(0);
        } lcnt++;

/* ignore comments */
        if(line[0] == '#')
            continue;

/* skip blank lines */
        if(strlen(line) <= 2) continue;

/* find out which parameter to set */
        if(sscanf(line,"%s",cmd) != 1)
            goto badline;
```

```c
        /* identify the parameter and scan for arguments */
        p = line + strlen(cmd);
        if(!strcmp(cmd,"frequency")) {
            if(sscanf(p,"%lf",&dtmp) != 1) goto badline;
            if(dtmp < 1.0 || dtmp > 50e3) goto badline;
            freq = dtmp;
            continue;
        } else if(!strcmp(cmd,"fname")) {
            if(sscanf(p,"%s",ptmp) != 1) goto badline;
            strcpy(fname,ptmp);
            continue;
        } else if(!strcmp(cmd,"save")) {
            save = 1;
            continue;
        } else if(!strcmp(cmd,"trunc")) {
            trunc = 1;
            continue;
        } else if(!strcmp(cmd,"process")) {
            process = 1;
            continue;
        } else if(!strcmp(cmd,"max")) {
            if(sscanf(p,"%d",&tmp) != 1) goto badline;
            if(tmp < 0) goto badline;
            max = tmp;
            continue;
        } else if(!strcmp(cmd,"order")) {
            if(sscanf(p,"%d",&tmp) != 1) goto badline;
            if(tmp < 0 || tmp > 100) goto badline;
            order = tmp;
            continue;
        } else if(!strcmp(cmd,"adc_gain")) {
            if(sscanf(p,"%d",&tmp) != 1) goto badline;
            if(tmp != 1 && tmp != 2 && tmp != 4 && tmp != 8) goto badline;
            adc_gain = tmp;
            continue;
        } else if(!strcmp(cmd,"threshold")) {
            if(sscanf(p,"%d",&tmp) != 1) goto badline;
            if(tmp < 0 || tmp > 4095) goto badline;
            threshold = tmp;
            continue;
        } badline:
        disp_text(22,5,"line ");
        printf("%d: %s",lcnt,line);
        sprintf(ptmp,"bad parameter on line %d in configuration file. (hit <CR>)",lcnt);
        prompt_line(ptmp);
        putch('\a');
        getch();
        clr_line(22);
        prompt_line("setting parameters from configuration file...");

}
} int load_idx()
{
FILE *fp;
int i,j;
static char idx_fname[13] = "cap.idx";
char ptmp[80],line[80];
int *idx;
```

```c
    prompt_line("opening index weighting file...");
    fp = fopen(idx_fname,"r");
    if(!fp) {
        sprintf(ptmp,"unable to open index weighting file: %s (hit <CR>)",
            idx_fname);
        prompt_line(ptmp);
        putch('\007');
        getch();
        return(-1);
    } prompt_line("reading index weights...");
    for(j = 0; j < 3; j++) {
        if(j == 0) idx = index1;
        else if(j == 1) idx = index2;
        else if(j == 2) idx = index3;
        for(i = 0; i < 10; i++) {
            if(feof(fp)) {
                prompt_line("error reading index weighting file: reached eof (hit <CR>");
                putch('\007');
                getch();
                return(-1);
            }
            fgets(line,80,fp);
            if(sscanf(line,"%d",idx + i) != 1) {
                prompt_line("error reading index weighting file: bad number (hit <CR>");
                putch('\007');
                getch();
                return(-1);
            }
        }
    }
``` display_parameters(capmain.c)

```c
    fclose(fp);

return(0);

}
``` display_parameters

```c
display_parameters()
{
    disp_text(3,1,"Parameters:");

disp_text(5,1,"Sample Frequency: ");
    printf("%6.11f Hz",freq);

disp_text(5,31,"Filter Order: ");
    printf("%d  A/D Gain: %d",order,adc_gain);

disp_text(6,1,"Save File Name: ");
    printf("%s\n",fname[0] ? fname : "(None)");

printf("Save Mode is: %s   File Mode is: %s",
        save ? "active" : "inactive",
        trunc ? "truncate" : "append");

disp_text(8,1,"plot maximum: ");
    if(max)
        printf("%-9d",max);
    else
        printf("autoscale");
```

```c
        printf("  out-of-balance threshold: %d",threshold);

disp_text(9,1,"display ");
        if(process)
            printf("processed data");
        else
            printf("raw data      ");
} int menu3()
{
unsigned tmp;
double dtmp;
char ch;
char ptmp[80];

while(1) {
        clr_to_bottom(4);
        display_parameters();
        disp_text(12,5,"Parameter Options:");
        disp_text(13,10,"1. Set Plotting Maximum");
        disp_text(14,10,"2. Toggle Processed/Raw Display");
``` display_parameters(capmain.c)

```c
        disp_text(15,10,"3. Enter Save-File Name");
        disp_text(16,10,"4. Toggle Save-File Write Mode");
        disp_text(17,10,"5. Toggle Save-to-Disk Mode");
        disp_text(18,10,"6. Set Sample Frequency");
        disp_text(19,10,"7. Set Filter Order");
        disp_text(20,10,"8. Set A/D Gain");
        disp_text(21,10,"9. Set Out-of-balance Threshold");

prompt_line("select a number, or <ESC> to return to main menu");
        do {
            ch = getch();
            if(ch == '\033') {
                return(0);
            }
        } while((ch < '1') || (ch > '9'));

switch(ch) {
            case '1':
                prompt_line("please enter the maximum plot value (0=autoscale): ");
                gets(ptmp);
                if(sscanf(ptmp,"%d",&tmp) != 1) {
                    putch('\007');
                    continue;
                }
                max = tmp;
                continue;
            case '2':
                process = !process;
                continue;
            case '3':
                prompt_line("please enter file name: ");
                gets(ptmp);
                if(sscanf(ptmp,"%s",fname) != 1) {
                    save = 0;
                    putch('\007');
                    continue;
                }
                continue;
```

```c
case '4':
    if(trunc == 1) trunc = 0; else trunc = 1;
    continue;
case '5':
    if(!fname[0]) {
        putch('\007');
        continue;
    }
    save = !save;
    continue;
case '6':
    prompt_line("please enter sample frequency (0.5 to 50e3): ");
    gets(ptmp);
    if(sscanf(ptmp,"%lf",&dtmp) != 1) {
        putch('\007');
``` display_parameters-main(capmain.c)

```c
        continue;
    }
    freq = dtmp;
    continue;
case '7':
    prompt_line("please enter filter order (1 to 100): ");
    gets(ptmp);
    if(sscanf(ptmp,"%d",&tmp) != 1) {
        putch('\007');
        continue;
    }
    order = tmp;
    continue;
case '8':
    prompt_line("please enter A/D gain (1, 2, 4, or 8): ");
    gets(ptmp);
    if(sscanf(ptmp,"%d",&tmp) != 1) {
        putch('\007');
        continue;
    }
    if(tmp != 1 && tmp != 2 && tmp != 4 && tmp != 8) {
        putch('\007');
        continue;
    }
    adc_gain = tmp;
    continue;
case '9':
    prompt_line("please enter out-of-balance threshold (0 to 4095):");
    gets(ptmp);
    if(sscanf(ptmp,"%d",&tmp) != 1) {
        putch('\007');
        continue;
    }
    if(tmp < 0 || tmp > 4095) {
        putch('\007');
        continue;
    }
    threshold = tmp;
    }
  }
}
``` main

```c
main(argc,argv)
int argc;
char *argv[];
{
int i,params_read;
char ch;

fname[0] = 0;
    bs = 0;
    params_read = 0;

while(1) {
        close_graphics();
        clr_disp();
        disp_text(1,1,"CAP - Capture and Display Can Defect Data  version 4.21");
        mv_curs(2,1);
        for(i = 0; i < 4; i++)
            printf("====================");
        display_parameters();
        disp_text(12,5,"Options:");
        disp_text(13,20,"1. Balance Coil");
        disp_text(14,20,"2. Capture Data");
        disp_text(15,20,"3. Set Parameters");

if(!params_read) {
            params_read = 1;
            load_cfg();
            load_idx();
            continue;
        } prompt_line("select a number, or <ESC> to quit");
        do {
            ch = getch();
            if(ch == '\033') {
                prompt_line("exiting");
                exit(0);
            }
        } while((ch < '1') || (ch > '3'));

switch(ch) {
            case '1':
                balance_coil();
                continue;
            /* case 2 is capture mode */
            case '3':
                menu3();
                continue;
        } if(ch != '2') {
            prompt_line("this option not implemented yet. (hit <CR>)");
            getch();
            continue;
        } init_adc_polled(freq,adc_gain);
        capture_mode(fname,save,trunc,max,process);
    }
}
```

(dt2821.c)

```c
/* vi: set autoindent showmatch : */
#include "dt2821.h"

/*
 * INIT_ADC - set up DT2821 to sample channel 0. If extclk is true, clock
 *            source is external; if int_err is true, the card will cause an
 *            interrupt on error; if int_ad is true, the card will interrupt
 *            on A/D conversion completion.
 */ unsigned init0,init1,init2,init3,init4;
unsigned trig;

void init_adc_polled(clkrt,gain)
double clkrt;
int gain;
{
static int int_err=0;
static int int_ad=0;

/* set the clock rate */
        if(clkrt)
            set_clock(clkrt);
        else
            set_clock(1000.0);

/* initialize the a/d system and clr dma done */
        init0 = CLRDMADONE | BUFFB | ADCINIT;

/* set RAM channel-gain list to 1 channel, channel 0 */
        init1 = LLE;

/* enable A/D clk, interrupt on A/D done(if int_ad), set gain to 8 */
        init2 = ADCLK | (int_ad?IADDONE:0);
        switch(gain) {
            case 1: init2 |= GS_1; break;
            case 2: init2 |= GS_2; break;
            case 4: init2 |= GS_4; break;
            case 8: init2 |= GS_8; break;
            default: init2 |= GS_1;
        }

/* done with setup; disable writes to RAM channel gain list */
        init3 = 0x0000;

/* select clock source, non-DMA, int. on error (if int_err), chan. 0 */
        init4 = (int_err?ERRINTEN:0)|DS_NONE|PRLD;

trig = STRIG | (int_err?ERRINTEN:0);
} void init_adc_dma(clkrt,gain)
double clkrt;
int gain;
{
int t;

/* set the clock rate */
        if(clkrt)
            set_clock(clkrt);
        else
            set_clock(1000.0);
```

```c
/* initialize the a/d system and clr dma done */
init0 = CLRDMADONE | BUFFB | ADCINIT;

/* set RAM channel-gain list to 1 channel, channel 0 */
init1 = LLE;

/* enable A/D clk, set gain to the requested value */
switch(gain) {
    case 1:
        t = GS_1;
        break;
    case 2:
        t = GS_2;
        break;
    case 4:
        t = GS_4;
        break;
    case 8:
        t = GS_8;
        break;
    default:
        return;
} init2 = ADCLK | t;

/* done with setup; disable writes to RAM channel gain list */
init3 = 0x0000;

/* select clock source, non-DMA, int. on error (if int_err), chan. 0 */
init4 = DS_NONE|PRLD;

trig = STRIG;
}

/* SET_CLOCK - sets the ADC clock to the closest possible frequency f */
int set_clock(f)
double f;
{
double x,powtwo;
int pre,cnt;

/* check for valid range */
    if(f < 0.5 || f > 50e4)
        return(-1);

/* find the lowest prescale and counter values to closely match f */
    powtwo = 1.0;
    pre = -1;
    do {
        x = 255.0 - (4e6 / powtwo) / f;
        pre++;
        powtwo *= 2.0;
    } while(pre < 16 && (x < 0.0 || x > 255.0));

if(pre == 16) return(-1);

/* round x to nearest value */
    cnt = (int)(x + 0.5);

/* set the timer/counter register */
    outpw(TMRCTR,(pre << 8) | cnt);
```

```
        return(0);
} void setup_conversion()
{
        /* initialize the a/d system and clr dma done */
        outpw(SUPCSR,init0);

/* set RAM channel-gain list to 1 channel, channel 0 */
        outpw(CHANCSR,init1);

/* enable A/D clk, interrupt on A/D done(if int_ad), set gain to 1 */
        outpw(ADCSR,init2);

/* done with setup; disable writes to RAM channel gain list */
        outpw(CHANCSR,init3);

/* select clock source, non-DMA, int. on error (if int_err), chan. 0 */
        outpw(SUPCSR,init4);

/* wait for the mux to settle on channel 0 */
        while(inpw(ADCSR) & MUXBUSY);
} int sample_adc(v)
int *v;
{
unsigned status;

setup_conversion();

/* trigger A/D */
        outpw(SUPCSR,trig);

/* wait for A/D done or error */
        while(!((status = inpw(ADCSR)) & (ADDONE | ADERR)));

/* check for error */
        /*if(status & ADERR) return(-1);*/

/* return the sample */
        *v = inpw(ADDAT) & ADDATA_MSK;

return(0);
} int read_buffer(b,n)
int *b,*n;
{
register unsigned s1,s2;

*n = 0;

setup_conversion();

/* set up to read from port 0; write to port 1 */
        outpw(DACSR,BBOE);

/* wait for can to leave coil before starting */
        while((inpw(DIODAT) & 0x0001) && !kbhit());
```

```c
        /* wait for can to enter coil before starting */
        while(!(inpw(DIODAT) & 0x0001) && !kbhit());

/* abort if key pressed */
        if(kbhit()) return(-2);

/* enable clock from black box */
        outpw(DIODAT,0x0100);

/* take samples until can leaves coil */
        do {
            /* trigger A/D */
            outpw(SUPCSR,trig);

/* wait for A/D done or error */
            while((s2 = (inpw(DIODAT) & 0x0001)) &&
                !((s1 = inpw(ADCSR)) & (ADDONE|ADERR)));

#if 0
            /* check for error */
            if((s1 & ADERR) && s2) {

/* disable black box clock */
            outpw(DIODAT,0x0000);
            return(-1);
            }
endif /* read the sample into the next location in the buffer */
            *(b++) = inpw(ADDAT);
            (*n)++;

/* setup for the next conversion */
            outpw(ADCSR,init2);
            outpw(SUPCSR,init4);

/* wait for the mux to settle on channel 0 */
            while((inpw(ADCSR) & MUXBUSY));
        } while(s2);

/* disable black box clock */
        outpw(DIODAT,0x0000);

/* abort if key was pressed */
        if(kbhit()) return(-2);

return(0);
} ifdef DEBUG
void read_dt2821_regs(s)
char *s;
{
unsigned w,v;
#define bit_on(x) ((x)?1:0)

printf("\n%s\n",s);
        printf("ADCSR:  %04x\n",w=inpw(ADCSR));
        printf("    ADERR:  %d\n",bit_on(w&ADERR));
        printf("    ADCLK:  %d\n",bit_on(w&ADCLK));
        printf("    MUXBUSY:%d\n",bit_on(w&MUXBUSY));
        printf("    ADDONE: %d\n",bit_on(w&ADDONE));
```

```
        printf("   IADDONE:%d\n",bit_on(w&IADDONE));
        printf("   GS bits:%d%d\n",bit_on(w&GS_4),bit_on(w&GS_2));
        printf("   channel:%d\n",w&CHAN_MSK);

printf("CHANCSR:%04x\n",w=inpw(CHANCSR));
        printf("   LLE    :%d\n",bit_on(w&LLE));
        printf("   PRESELA:%d\n",(w&PRESELA_MSK)>>8);
        printf("   NUMB   :%d\n",w&NUMB_MSK);

printf("ADDAT:  %04x\n",w=inpw(ADDAT));

printf("DACSR:  %04x\n",w=inpw(DACSR));
        printf("   DAERR  :%d\n",bit_on(w&DAERR));
        printf("   YSEL   :%d\n",bit_on(w&YSEL));
        printf("   SSEL   :%d\n",bit_on(w&SSEL));
        printf("   DACRDY :%d\n",bit_on(w&DACRDY));
        printf("   IDARDY :%d\n",bit_on(w&IDARDY));
        printf("   DACLK  :%d\n",bit_on(w&DACLK));
        printf("   HBOE   :%d\n",bit_on(w&HBOE));
        printf("   LBOE   :%d\n",bit_on(w&LBOE));

printf("DADAT:  %04x\n",w=inpw(DADAT));

printf("DIODAT: %04x\n",w=inpw(DIODAT));

printf("SUPCSR: %04x\n",w=inpw(SUPCSR));
        printf("   DMAD   :%d\n",bit_on(w&DMAD));
        printf("   ERRINTEN:%d\n",bit_on(w&ERRINTEN));
        printf("   CLRDMAD:%d\n",bit_on(w&CLRDMADONE));
        printf("   DDMA   :%d\n",bit_on(w&DDMA));
        printf("   DMAMODE:%d%d\n",bit_on(w&DS_DACLK),bit_on(w&DS_ADCLK));
        printf("   BUFFB  :%d\n",bit_on(w&BUFFB));
        printf("   SCDN   :%d\n",bit_on(w&SCDN));
        printf("   DACON  :%d\n",bit_on(w&DACON));
        printf("   ADCINIT:%d\n",bit_on(w&ADCINIT));
        printf("   DACINIT:%d\n",bit_on(w&DACINIT));
        printf("   PRLD   :%d\n",bit_on(w&PRLD));
        printf("   STRIG  :%d\n",bit_on(w&STRIG));
        printf("   XTRIG  :%d\n",bit_on(w&XTRIG));
        printf("   XCLK   :%d\n",bit_on(w&XCLK));
        printf("   BDINIT :%d\n",bit_on(w&BDINIT));

printf("TMRCTR: %04x\n",w=inpw(TMRCTR));
}
endif
```

(graph.c)

```
include <graph.h> static struct videoconfig vc;
static int px,py,xhalf,yhalf;
static int nx,ny,minx,maxx,miny,maxy,th,tw;

#define XO 25
#define YO (PYMAX + th + 1)
define PYMAX 30 int open_graphics()
{
```

```
#if 0
        sprintf(ptmp,"Threshold: %d",threshold);
        _settextposition(TSCALE(YO-PYMAX),vc.numtextcols/2 - strlen(ptmp)/2);
        _outtext(ptmp);
endif /* draw the box */
        _setcolor(4);
        _moveto(0,YO - PYMAX);
        _lineto(px - 1, YO - PYMAX);
        _lineto(px - 1, YO + PYMAX);
        _lineto(0,YO + PYMAX);
        _lineto(0,YO - PYMAX);
        _setcolor(7);

} if 0
int y_scale(y)
int y;
{
double yh,ym,tres;
int y_max;
        yh = yhalf;
        ym = y_max;
        tres = (yh/ym) * (double)y;
        return(yhalf + (int)tres);
}
endif
int plot(buf,n,smax)
int *buf;
int n,smax;
{
register int i,ymax,ymin;
double step,ys;
char ptmp[60];
int max;

#define YSCALE(y) (YO - (int)((double)(y)*ys))

/* find minimum value and maximum value */
        ymax = 0;
        ymin = 4096;
        for(i = 0; i < n; i++) {
            if(buf[i] > ymax) ymax = buf[i];
            if(buf[i] < ymin) ymin = buf[i];
        } if(!smax)
            max = (abs(ymax) > abs(ymin) ? abs(ymax) : abs(ymin));
        else
            max = smax;

if(max)
            ys = (double)PYMAX/(double)max;
        else
            ys = (double)PYMAX;
        step = (double)(px - 10 - XO) / (double)n;

axes(n,max);

_setcolor(2);
        _moveto(XO,YSCALE(buf[0]));
```

```
        /* _setvideomode(_ERESCOLOR); */
        if(!_setvideomode(_HRESBW)) {
            prompt_line("unable to set graphics mode (hit <CR>)");
            getch();
            exit(1);
        }
        _getvideoconfig(&vc);
        px = vc.numxpixels;
        py = vc.numypixels;
        tw = px / vc.numtextcols;
        th = px / vc.numtextrows;
        xhalf = px / 2;
        yhalf = py / 2;
        _clearscreen(_GCLEARSCREEN);
} int close_graphics()
{
        _setvideomode(_DEFAULTMODE);
} int axes(xmax,ymax)
int xmax,ymax;
{
int i;
char ptmp[40];

/*#define TSCALE(y) ((int)(1+((float)(vc.numtextrows-1.0)/(float)py)*(float)(y)))*/
#define TSCALE(y) ((int)(((float)(vc.numtextrows-1.0)/(float)py)*(float)(y)))

/* initialize the plotting variables */
        nx = px - 10 - XO;
        ny = 2 * PYMAX;
        minx = 0;
        miny = -ymax;
        maxx = xmax;
        maxy = ymax;

#if 0
        /* draw the axes */
        _moveto(XO,YO);
        _lineto(px - 10,YO);
        _moveto(XO,YO - PYMAX);
        _lineto(XO,YO + PYMAX);
endif /* label the axes */
        _settextposition(TSCALE(YO)+1,2);
        _outtext("0");

sprintf(ptmp,"%d",maxx);
        _settextposition(TSCALE(YO)+1,vc.numtextcols - strlen(ptmp));
        _outtext(ptmp);

sprintf(ptmp,"%d",miny);
        _settextposition(TSCALE(YO+PYMAX)+2,1);
        _outtext(ptmp);

sprintf(ptmp,"%d",maxy);
        _settextposition(TSCALE(YO-PYMAX),1);
        _outtext(ptmp);
```

```
        for(i = 1; i < n; i++)
            _lineto((int)(XO + i*step),YSCALE(buf[i]));
        _setcolor(7);

sprintf(ptmp,"Max: %d    Min: %d",ymax,ymin);
        gdisp_text(20,5,ptmp);
} int gmv_curs(r,c)
int r,c;
{
        _settextposition(r,c);
} int gclr_line(r)
int r;
{
static char ptmp[21] = "                    ";
        _settextposition(r,1);
        _outtext(ptmp);
        _outtext(ptmp);
        _outtext(ptmp);
        _outtext(ptmp);
} int gprompt_line(s)
char *s;
{
        gcenter_text(24,s);
} int gdisp_text(r,c,s)
int r,c;
char *s;
{
        _settextposition(r,c);
        _outtext(s);
} int gcenter_text(r,s)
int r;
char *s;
{
        gclr_line(r);
        _settextposition(r,40-strlen(s)/2);
        _outtext(s);
} int gclr_disp()
{
        _clearscreen(_GCLEARSCREEN);
}
```

What is claimed is:

1. Apparatus for detecting surface flaws in cylindrical articles having central longitudinal axes, comprising:
   a) guide means for guiding said cylindrical articles along a displacement path having a central longitudinal axis extending coaxially of said central longitudinal axes of said articles; and
   b) a detection coil assembly positioned in annular relationship with said displacement path for producing a signal representative of the surface geometry of a cylindrical article which traverses said displacement path comprising:
   i) a first spool assembly including a first bifilar winding pair comprising a first and second winding; said first winding comprising first field generating coil means having a central longitudinal coil axis positioned coaxially of said displacement path central longitudinal axis for generating a first magnetic field for inducing eddy currents in cylindrical articles passed axially through said first field generating coil means; said second winding comprising first sensor coil means for generating a first sensor coil signal representative of the flux of said first magnetic field;

ii) a second spool assembly axially spaced from said first spool assembly and including a second bifilar winding pair comprising a third and fourth winding; said third winding comprising a second field generating coil means having a central longitudinal coil axis positioned coaxially of said displacement path central longitudinal axis for generating a second magnetic field for inducing eddy currents in cylindrical articles passed axially through said second field generating coil means; said fourth winding comprising a second sensor coil means for generating a second sensor coil signal representative of the flux of said second magnetic field;

iii) ferromagnetic spacer means positioned between said first and second spool assemblies for isolating said first magnetic field from said second magnetic field; and c) signal processing means for processing said first sensor coil signal in relationship to said second sensor coil signal and for generating a signal representative of the difference between said first and second sensor coil signals.

2. The invention of claim 1 further comprising: first excitation means connected to said first field generating coil means for passing a first alternating electrical current through said first field generating coil means;

second excitation means connected to said second field generating coil means for passing a second alternating electrical current through said second field generating coil means; and said first alternating current being in same phase relationship with said second alternating current.

3. The invention of claim 2 wherein said signal processing means for processing said first sensor coil signal with respect to said second sensor coil signal comprises a bridge circuit including said first and second sensor coil means.

4. The invention of claim 1 said signal processing means further comprising:

article detector means for detecting the presence or absence of a cylindrical article within a predetermined length of said displacement path and for generating a signal representative thereof.

5. The invention of claim 4, said article detector means comprising:

a first photo detector assembly positioned along said displacement path upstream of said first and second coil means; and a second photo detector assembly positioned along said displacement path downstream of said first and second coil means.

6. The invention of claim 1 further comprising display means for displaying data representative of the surface geometry of an article passed along said displacement path.

7. The invention of claim 1 further comprising data storage means for storing data representative of the surface geometry of an article passed along said displacement path.

* * * * *